United States Patent
Wakamatsu et al.

(10) Patent No.: US 9,708,341 B2
(45) Date of Patent: Jul. 18, 2017

(54) METHOD FOR PRODUCING PYRIDINE COMPOUND

(71) Applicant: Sumitomo Chemical Company, Limited, Tokyo (JP)

(72) Inventors: Takayuki Wakamatsu, Oita (JP); Rika Kasai, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/316,603

(22) PCT Filed: May 29, 2015

(86) PCT No.: PCT/JP2015/065512
§ 371 (c)(1),
(2) Date: Dec. 6, 2016

(87) PCT Pub. No.: WO2015/190316
PCT Pub. Date: Dec. 17, 2015

(65) Prior Publication Data
US 2017/0152270 A1    Jun. 1, 2017

(30) Foreign Application Priority Data
Jun. 9, 2014    (JP) ................................ 2014-118457

(51) Int. Cl.
| | | |
|---|---|---|
| *C07D 471/04* | (2006.01) | |
| *C07D 413/04* | (2006.01) | |
| *C07D 417/04* | (2006.01) | |
| *C07D 401/04* | (2006.01) | |
| *C07D 498/04* | (2006.01) | |
| *C07D 413/12* | (2006.01) | |
| *C07D 401/12* | (2006.01) | |
| *C07D 417/12* | (2006.01) | |

(52) U.S. Cl.
CPC ......... *C07D 498/04* (2013.01); *C07D 401/12* (2013.01); *C07D 413/12* (2013.01); *C07D 417/12* (2013.01); *C07D 471/04* (2013.01)

(58) Field of Classification Search
CPC .. C07D 413/04; C07D 471/04; C07D 417/04; C07D 401/04
USPC .................. 546/118, 270.1, 271.7, 273.4
See application file for complete search history.

(56) References Cited

U.S. PATENT DOCUMENTS

| | | |
|---|---|---|
| 6,262,273 B1 | 7/2001 | Hamprecht et al. |
| 2008/0039464 A1 | 2/2008 | Berry et al. |
| 2008/0269210 A1 | 10/2008 | Castanedo et al. |
| 2011/0071175 A1 | 3/2011 | Hynd et al. |
| 2014/0194290 A1 | 7/2014 | Takahashi et al. |

FOREIGN PATENT DOCUMENTS

| | | |
|---|---|---|
| JP | 2001500141 A | 1/2001 |
| JP | 2009544755 A | 12/2009 |
| JP | 2010512337 A | 4/2010 |
| JP | 2011506415 A | 3/2011 |
| JP | 2014005263 A | 1/2014 |
| WO | 2013018928 A1 | 2/2013 |

OTHER PUBLICATIONS

Maruzen Co., Ltd., "Jikken Kagaku Koza 24," Yuki Gosei, Ed. 4, No. 5, pp. 366-367 (Sep. 25, 1992).
Int'l Preliminary Report on Patentability issued Dec. 15, 2016 in Int'l Application No. PCT/JP2015/065512.
Int'l Search Report issued Jul. 21, 2015 in Int'l Application No. PCT/JP2015/065512.

*Primary Examiner* — Patricia L Morris
(74) *Attorney, Agent, or Firm* — Panitch Schwarze Belisario & Nadel LLP

(57) ABSTRACT

A pyridine compound represented by formula (1) that is useful as an insecticide is produced by reacting a compound represented by formula (2) and a compound represented by formula (3). In formula (2) $L^1$ represents a halogen atom; $R^2$, $R^3$, $R^4$, $R^5$, and $R^6$ represent chain hydrocarbon groups, etc., having 1-6 carbon atoms optionally substituted by fluorine atoms; $A^1$ represents $-NR^7-$, an oxygen atom, or a sulfur atom; $A^2$ represents a nitrogen atom or $=CR^8-$; and $R^7$ and $R^8$ represent C1-6 chain hydrocarbon groups or hydrogen atoms. In formula (3) $M^+$ represents a sodium ion, a potassium ion, or a lithium ion.

7 Claims, 1 Drawing Sheet

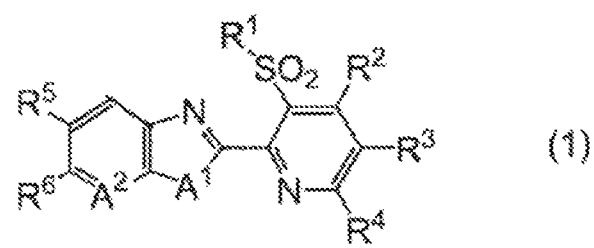
(1)
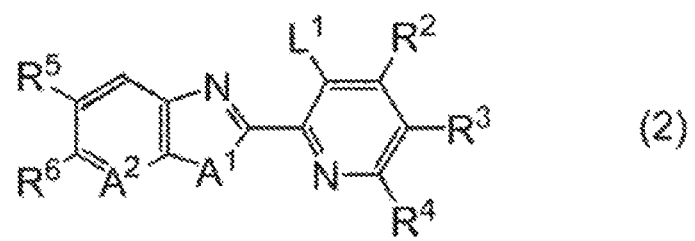
(2)
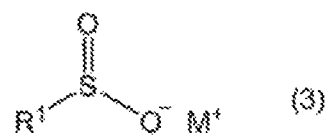
(3)

METHOD FOR PRODUCING PYRIDINE COMPOUND

CROSS-REFERENCE TO RELATED APPLICATION

This application is a Section 371 of International Application No. PCT/JP2015/065512, filed May 29, 2015, which was published in the Japanese language on Dec. 17, 2015, under International Publication No. WO 2015/190316 A1, and the disclosure of which is incorporated herein by reference.

TECHNICAL FIELD

The present invention relates to a method for preparing a pyridine compound.

BACKGROUND ART

WO 2013/018928 discloses a pyridine compound such as 2-(3-ethylsulfonyl-5-pentafluoroethylpyridin-2-yl)-3-methyl-6-trifluoromethyl-3H-imidazo[4,5-b]pyridine represented by the following formula:

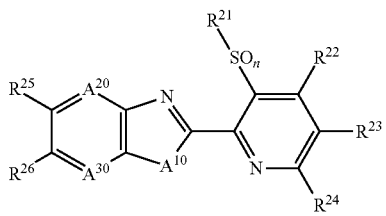

wherein
$A^{10}$ represents $-NR^{27}-$, an oxygen atom, or a sulfur atom,
$A^{20}$ represents a nitrogen atom or $=CR^{28}-$,
$A^{30}$ represents a nitrogen atom or $=CR^{29}-$,
$R^{21}$ represents a chain hydrocarbon group with one to six carbons which may optionally have substituent(s) or an alicyclic hydrocarbon group with three to six carbons which may optionally have substituent(s),
$R^{22}$, $R^{23}$, and $R^{24}$ represent each independently a chain hydrocarbon group with one to six carbons which may optionally have substituent(s), a phenyl group which may optionally have substituent(s), a 5- or 6-membered heterocyclic group which may optionally have substituent(s), $-OR^{30}$, $-S(O)_mR^{30}$, $-S(O)_2NR^{30}R^{40}$, $-NR^{30}R^{40}$, $-NR^{30}CO_2R^{40}$, $-NR^{30}C(O)R^{40}$, $-CO_2R^{30}$, $-C(O)R^{30}$, $-C(O)NR^{30}R^{40}$, $-SF_5$, a cyano group, a nitro group, a halogen atom, or a hydrogen atom,
$R^{25}$ and $R^{26}$ represent each independently a chain hydrocarbon group with one to six carbons which may optionally have substituent(s), a phenyl group which may optionally have substituent(s), a 5- or 6-membered heterocyclic group which may optionally have substituent(s), $-OR^{30}$, $-S(O)_mR^{30}$, $-S(O)_2NR^{30}R^{40}$, $-NR^{30}R^{40}$, $-NR^{30}CO_2R^{40}$, $-NR^{30}C(O)R^{40}$, $-CO_2R^{30}$, $-C(O) R^{30}$, $-C(O) NR^{30}R^{40}$, $-SF_5$, a cyano group, a nitro group, a halogen atom, or a hydrogen atom, provided that both $R^{25}$ and $R^{26}$ are not a hydrogen atom,
m is an integer of 0-2,
n is an integer of 0-2,
$R^{30}$ and $R^{40}$ represent each independently a chain hydrocarbon group with one to six carbons which may optionally have substituent(s), a phenyl group which may optionally have substituent(s), or a hydrogen atom,
$R^{27}$ represents a chain hydrocarbon group with one to six carbons which may optionally have substituent(s), $-CO_2R^{30}$, $-C(O)R^{30}$, an alicyclic hydrocarbon group with three to six carbons which may optionally have substituent(s), or a hydrogen atom, and
$R^{28}$ and $R^{29}$ represent each independently a chain hydrocarbon group with one to six carbons which may optionally have halogen atom(s), $-OR^{30}$, $-S(O)_mR^{30}$, $-NR^{30}R^{40}$, $-CO_2R^{30}$, $-C(O) R^3$, a cyano group, a nitro group, a halogen atom, or a hydrogen atom,
which is useful as an insecticide.

WO 2013/018928 discloses a process for preparing 2-(3-ethylsulfonyl-5-pentafluoroethylpyridin-2-yl)-3-methyl-6-trifluoromethyl-3H-imidazo[4,5-b]pyridine, which comprises oxidizing 2-(3-ethylsulfanyl-5-pentafluoroethylpyridin-2-yl)-3-methyl-6-trifluoromethyl-3H-imidazo[4,5-b]pyridine with m-chloroperoxybenzoic acid.

SUMMARY OF THE INVENTION

The present invention is to provide a novel method for preparing the pyridine compound described above and includes the following inventions.

[1] A method for preparing a pyridine compound of formula (1):

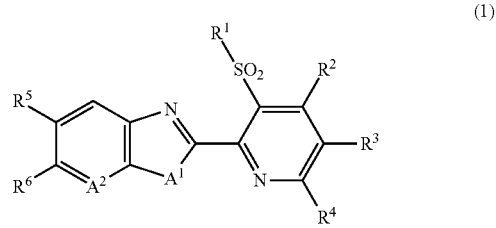

which comprises reacting a compound of formula (2):

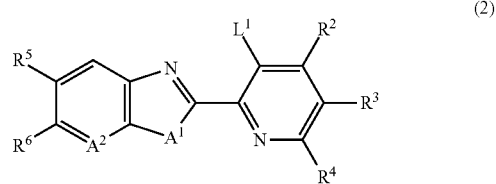

wherein
$L^1$ represents a halogen atom,
$R^2$, $R^3$, $R^4$, $R^5$, and $R^6$ represent each independently a chain hydrocarbon group having one to six carbons which may be optionally substituted with fluorine atom(s), a phenyl group which may optionally have substituent(s), $-OR^{10}$, $-S(O)_mR^{10}$, $-S(O)_2NR^{11}R^{12}$, $-NR^{10}R^{13}$, $-NR^{11}CO_2R^3$, $-NR^{11}C(O)R^{12}$, $-CO_2R^{10}$, $-C(O)R^{11}$, $-C(O)NR^{11}R^{12}$, $-SF_5$, a cyano group, a nitro group, or a hydrogen atom,
m and n are each independently an integer of 0-2,
provided that both $R^5$ and $R^6$ are not a hydrogen atom, $R^{10}$ and $R^{13}$ represent each independently a chain hydrocarbon group having one to six carbons which may be optionally substituted with fluorine atom(s) or a phenyl group which may optionally have substituent(s), $R^{11}$ and $R^{12}$ represent each independently a chain hydrocarbon group having one to six carbons which may be optionally substituted with fluorine atom(s), a phenyl group which may optionally have substituent(s), or a hydrogen atom, $A^1$ represents —$NR^7$—, an oxygen atom, or a sulfur atom, $A^2$ represents a nitrogen atom or =$CR^8$—, and $R^7$ and $R^8$ represent each independently a chain hydrocarbon group having one to six carbons, or a hydrogen atom, wherein in the phenyl group which may optionally have substituent(s) as $R^2$, $R^3$, $R^4$, $R^5$, $R^6$, $R^{10}$, $R^{11}$, $R^{12}$, and $R^{13}$, the substituent(s) is/are one or more substituent(s) selected from the group consisting of a chain hydrocarbon group having one to six carbons which may be optionally substituted with fluorine atom(s), an alkoxy group having one to six carbons which may be optionally substituted with fluorine atom(s), an alkylthio group having one to six carbons which may be optionally substituted with fluorine atom(s), an alkylsulfinyl group having one to six carbons which may be optionally substituted with fluorine atom(s), an alkylsulfonyl group having one to six carbons which may be optionally substituted with fluorine atom(s), an alkylcarbonyl group having two to six carbons which may be optionally substituted with fluorine atom(s), an alkoxycarbonyl group having two to six carbons which may be optionally substituted with fluorine atom(s), a halogen atom, a cyano group, and a nitro group, with a compound of formula (3):

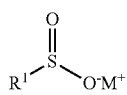

(3)

wherein $R^1$ represents a chain hydrocarbon group having one to six carbons which may be optionally substituted with fluorine atom(s) or an alicyclic hydrocarbon group having three to six carbons which may be optionally substituted with fluorine atom(s), and $M^+$ represents a sodium ion, a potassium ion, or a lithium ion, to prepare the compound of formula (1), wherein $R^1$, $R^2$, $R^3$, $R^4$, $R^5$, $R^6$, $A^1$, $A^2$, and $A^3$ have the same meanings as defined above.

[2] The method described in [1], wherein $R^2$ and $R^4$ represent a hydrogen atom, $R^3$ represents a hydrogen atom or a trifluoromethyl group, $R^5$ represents a trifluoromethyl group, a tetrafluoroethyl group, a trifluoromethylthio group, a trifluoromethylsulfinyl group, or a trifluoromethylsulfonyl group, $R^6$ represents a hydrogen group, and $A^2$ represents a nitrogen atom or =CH—.

[3] The method described in [2], wherein $A^1$ represents an oxygen atom, and $A^2$ represents =CH—.

[4] The method described in [2], wherein $A^1$ represents —$NR^7$—, $R^7$ represents a methyl group, and $A^2$ represents a nitrogen atom.

[5] The method described in [3], wherein $R^1$ represents a chain hydrocarbon group having one to six carbons.

[6] The method described in [4], wherein $R^1$ represents a chain hydrocarbon group having one to six carbons.

[7] The method described in any one of [1] to [6], wherein $L^1$ represents a fluorine atom or a chlorine atom.

EMBODIMENT FOR CARRYING OUT THE INVENTION

Examples of the halogen atom defined as $L^1$ include a fluorine atom, a chlorine atom, a bromine atom, or an iodine atom. Examples of a preferable halogen atom as $L^1$ include a fluorine atom or a chlorine atom.

Examples of the chain hydrocarbon group having one to six carbons which may be optionally substituted with fluorine atom(s) defined as $R^1$, $R^2$, $R^3$, $R^4$, $R^5$, $R^6$, $R^{10}$, $R^{11}$, $R^{12}$, and $R^{13}$ include an alkyl group having one to six carbons which may be optionally substituted with fluorine atom(s), an alkenyl group having two to six carbons which may be optionally substituted with fluorine atom(s), and an alkynyl group having two to six carbons which may be optionally substituted with fluorine atom(s).

Examples of the alkyl group having one to six carbons which may be optionally substituted with fluorine atom(s) include a methyl group, an ethyl group, a propyl group, an isopropyl group, a butyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, and a heptafluoroisopropyl group.

Examples of the alkenyl group having two to six carbons which may be optionally substituted with fluorine atom(s) include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group.

Examples of the alkynyl group having two to six carbons which may be optionally substituted with fluorine atom(s) include an ethynyl group, a propargyl group, a 2-butynyl group, a 3-butynyl group, a 1-pentynyl group, a 1-hexynyl group, and a 4,4,4-trifluoro-2-butynyl group.

The phenyl group defined as $R^1$, $R^2$, $R^3$, $R^4$, $R^5$, $R^6$, $R^{10}$, $R^{11}$, $R^{12}$, and $R^{13}$ may optionally have one or more substituent(s) selected from the following Group Z.

Group Z: a chain hydrocarbon group having one to six carbons which may be optionally substituted with fluorine atom(s), an alkoxy group having one to six carbons which may be optionally substituted with fluorine atom(s), an alkylthio group having one to six carbons which may be optionally substituted with fluorine atom(s), an alkylsulfinyl group having one to six carbons which may be optionally substituted with fluorine atom(s), an alkylsulfonyl group having one to six carbons which may be optionally substituted with fluorine atom(s), an alkylcarbonyl group having two to six carbon which may be optionally substituted with fluorine atom(s), an alkoxycarbonyl group having two to six carbons which may be optionally substituted with fluorine atom(s), a halogen atom (a fluorine atom, a chlorine atom, a bromine atom, an iodine atom), a cyano group, and a nitro group.

In the Group Z, an example of the chain hydrocarbon group having one to six carbons which may be optionally substituted with fluorine atom(s) is the same as that of the chain hydrocarbon group having one to six carbons which may be optionally substituted with fluorine atom(s) defined as $R^2$, $R^3$, $R^4$, $R^5$, and $R^6$.

Examples of the alkoxy group having one to six carbons which may be optionally substituted with fluorine atom(s)

include a methoxy group, a trifluoromethoxy group, an ethoxy group, a 2,2,2-trifluoroethoxy group, a propoxy group, an isopropoxy group, a butoxy group, an isobutoxy group, a sec-butoxy group, a tert-butoxy group, a pentyloxy group, and a hexyloxy group.

Examples of the alkylthio group having one to six carbons which may be optionally substituted with fluorine atom(s) include a methylthio group, an ethylthio group, a propylthio group, an isopropylthio group, a butylthio group, a sec-butylthio group, a tert-butylthio group, a pentylthio group, a hexylthio group, a trifluoromethylthio group, a 2,2,2-trifluoroethylthio group, and a pentafluoroethylthio group.

Examples of the alkylsulfinyl group having one to six carbons which may be optionally substituted with fluorine atom(s) include a methylsulfinyl group, an ethylsulfinyl group, a propylsulfinyl group, an isopropylsulfinyl group, a butylsulfinyl group, a pentylsulfinyl group, a hexylsulfinyl group, a trifluoromethylsulfinyl group, a 2,2,2-trifluoroethylsulfinyl group, and a pentafluoroethylsulfinyl group.

Examples of the alkylsulfonyl group having one to six carbons which may be optionally substituted with fluorine atom(s) include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a 2,2,2-trifluoroethylsulfonyl group, and a pentafluoroethylsulfonyl group.

Examples of the alkylcarbonyl group having two to six carbons which may be optionally substituted with fluorine atom(s) include an acetyl group, a propionyl group, a butyryl group, a pentanoyl group, a hexanoyl group, and a trifluoroacetyl group.

Examples of the alkoxycarbonyl group having two to six carbons which may be optionally substituted with fluorine atom(s) include a methoxycarbonyl group, an ethoxycarbonyl group, a propoxycarbonyl group, a butoxycarbonyl group, a pentyloxycarbonyl group, a tert-butoxycarbonyl group, and a 2,2,2-trifluoroethoxycarbonyl group.

Examples of the phenyl group which may optionally have one or more substituent(s) selected from the Group Z include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, a 2-trifluoromethoxyphenyl group, a 3-trifluoromethoxyphenyl group, a 4-trifluoromethoxyphenyl group, a 2-trifluoromethylsulfanylphenyl group, a 3-trifluoromethylsulfanylphenyl group, a 4-trifluoromethylsulfanylphenyl group, a 4-methoxycarbonylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-acetylphenyl group, and a 4-methoxycarbonylphenyl group.

Examples of the chain hydrocarbon group having one to six carbons defined as $R^7$ and $R^8$ include an alkyl group having one to six carbons, an alkenyl group having two to six carbons, and an alkynyl group having two to six carbons.

Examples of the alkyl group having one to six carbons include a methyl group, an ethyl group, a propyl group, an isopropyl group, a butyl group, a sec-butyl group, a tert-butyl group, a pentyl group, a neopentyl group, and a hexyl group.

Examples of the alkenyl group having two to six carbons include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, and a 1-hexenyl group.

Examples of the alkynyl group having two to six carbons include an ethynyl group, a propargyl group, a 2-butynyl group, a 3-butynyl group, a 1-pentynyl group, and a 1-hexynyl group.

Examples of the alicyclic hydrocarbon group having three to six carbons which may be optionally substituted with fluorine atom(s) defined as $R^1$ include a cyclopropyl group, a 1-methylcyclopropyl group, a 2-methylcyclopropyl group, a 1-fluorocyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

Examples of —$OR^{10}$ defined as $R^2$, $R^3$, $R^4$, $R^5$, and $R^6$ include an alkoxy group having one to six carbons such as methoxy group, trifluoromethoxy group, ethoxy group, 2,2,2-trifluoromethoxy group, propoxy group, butoxy group, isobutoxy group, sec-butoxy group, tert-butoxy group, pentyloxy group and hexyloxy group; an alkenyloxy group having two to six carbons such as vinyloxy group, 1-propenyloxy group, 2-propenyloxy group, 1-methylvinyloxy group, 2-methyl-1-propenyloxy group, 1-butenyloxy group, 2-butenyloxy group, 3-butenyloxy group, 1-pentenyloxy group and 1-hexenyloxy group; and an alkynyloxy group having two to six carbons such as ethynyloxy group, propargyloxy group, 2-butynyloxy group, 3-butynyloxy group, 1-pentynyloxy group and 1-hexynyloxy group.

Examples of "m" in —$S(O)_mR^{10}$ defined as $R^2$, $R^3$, $R^4$, $R^5$, and $R^6$ include an integer of 0-2, preferably, 1 or 2. Examples of $R^{10}$ in —$S(O)_mR^{10}$ include preferably an alkyl group having one to six carbons which may be optionally substituted with fluorine atom(s), more preferably a trifluoromethyl group.

Examples of —$S(O)_mR^{10}$ include an alkylthio group having one to six carbons such as methylthio group, ethylthio group, propylthio group, isopropylthio group, butylthio group, sec-butylthio group, tert-butylthio group, pentylthio group, neopentylthio group, hexylthio group, trifluoromethylthio group, 2,2,2-trifluoroethylthio group and pentafluoroethylthio group; an alkylsulfinyl group having one to six carbons such as methylsulfinyl group, ethylsulfinyl group, propylsulfinyl group, isopropylsulfinyl group, butylsulfinyl group, sec-butylsulfinyl group, tert-butylsulfinyl group, pentylsulfinyl group, neopentylsulfinyl group, hexylsulfinyl group, trifluoromethylsulfinyl group, 2,2,2-trifluoroethylsulfinyl group and pentafluoroethylsulfinyl group; and an alkylsulfonyl group having one to six carbons such as methylsulfonyl group, ethylsulfonyl group, propylsulfonyl group, isopropylsulfonyl group, butylsulfonyl group, sec-butylsulfonyl group, tert-butylsulfonyl group, pentylsulfonyl group, neopentylsulfonyl group, hexylsulfonyl group, trifluoromethylsulfonyl group, 2,2,2-trifluoroethylsulfonyl group and pentafluoroethylsulfonyl group.

Examples of —$S(O)_2NR^{11}R^{12}$ include an aminosulfonyl group; an alkylaminosulfonyl group having one to six carbons such as methylaminosulfonyl group, ethylaminosulfonyl group, propylaminosulfonyl group, butylaminosulfonyl group, pentylaminosulfonyl group and hexylaminosulfonyl group; and a dialkylaminosulfonyl group having two to twelve carbons such as dimethylaminosulfonyl group, diethylaminosulfonyl group, dipropylaminosulfonyl group, dibutylaminosulfonyl group, dipentylaminosulfonyl group, dihexylaminosulfonyl group and methylethylaminosulfonyl group.

Examples of —$NR^{10}R^{13}$ include an amino group having one to twelve carbons such as methylamino group, ethylamino group, propylamino group, butylamino group, pentylamino group, hexylamino group, dimethylamino group and diethylamino group.

Examples of —$NR^{11}CO_2R^{13}$ include a methoycarbonylamino group and an ethoxycarbonylamino group.

Examples of —$NR^{11}C(O)R^{12}$ include a methylcarbonylamino group.

Examples of —$CO_2R^{10}$ include an alkoxycarbonyl group having two to seven carbons such as methoxycarbonyl group, ethoxycarbonyl group, propoxycarbonyl group, isopropoxycarbonyl group, butoxycarbonyl group and pentyloxycarbonyl group; an alkenyloxycarbonyl group having three to seven carbons such as vinyloxycarbonyl group, 1-propenyloxycarbonyl group, 2-propenyloxycarbonyl group, 1-methylvinyloxycarbonyl group, 2-methyl-1-propenyloxycarbonyl group, 1-butenyloxycarbonyl group, 2-butenyloxycarbonyl group, 3-butenyloxycarbonyl group, 1-pentenyloxycarbonyl group and 1-hexenyloxycarbonyl group; and an alkynyloxycarbonyl group having three to seven carbons such as ethynyloxycarbonyl group, propargyloxycarbonyl group, 2-butynyloxycarbonyl group, 3-butynyloxycarbonyl group, 1-pentynyloxycarbonyl group and 1-hexynyloxycarbonyl group.

Examples of —$CO_2R^{11}$ include an alkylcarbonyl group having two to seven carbons such as methylcarbonyl group, ethylcarbonyl group, propylcarbonyl group, butylcarbonyl group and pentylcarbonyl group; an alkenylcarbonyl group such as vinylcarbonyl group, 1-propenylcarbonyl group, 2-propenylcarbonyl group, 1-methylvinylcarbonyl group, 2-methyl-1-propenylcarbonyl group, 1-butenylcarbonyl group, 2-butenylcarbonyl group, 3-butenylcarbonyl group, 1-pentenylcarbonyl group and 1-hexenylcarbonyl group; and an alkynylcarbonyl group having three to seven carbons such as ethynylcarbonyl group, propargylcarbonyl group, 2-butynylcarbonyl group, 3-butynylcarbonyl group, 1-pentynylcarbonyl group and 1-hexynylcarbonyl group.

Examples of —$C(O)NR^{11}R^{12}$ include an aminocarbonyl group having one to six carbons such as aminocarbonyl group, methylaminocarbonyl group, dimethylaminocarbonyl group and methylethylaminocarbonyl group.

$R^2$, $R^3$, and $R^4$ represent each independently, preferably a hydrogen atom or a chain hydrocarbon group having one to six carbons which may be optionally substituted with fluorine atom(s), more preferably a hydrogen atom or an alkyl group having one to six carbons which may optionally have halogen atom(s), even more preferably a trifluoromethyl group, a tetrafluoroethyl group, or a hydrogen atom, and the most preferably a hydrogen atom.

$A^1$ represents preferably —$NR^7$— or an oxygen atom.

$A^2$ represents preferably =$CR^8$—, more preferably =$CR^8$- wherein $R^8$ represents a hydrogen atom or an alkyl group having one to six carbons, and even more preferably =CH—.

A compound represented by formula (2) (hereinafter, referred to as "Compound (2)") is recited as the compounds represented by the formulae (2-1) to (2-39) in Table 1.

TABLE 1

| Compound | $R^2$ | $R^3$ | $R^4$ | $R^5$ | $R^6$ | $A^1$ | $A^2$ | $L^1$ |
|---|---|---|---|---|---|---|---|---|
| 2-1 | H | H | H | $SO_2CF_3$ | H | O | CH | F |
| 2-2 | H | H | H | $SOCF_3$ | H | O | CH | F |
| 2-3 | H | H | H | $SCF_3$ | H | O | CH | F |
| 2-4 | H | $CF_3$ | H | $CF_2CF_3$ | H | $NCH_3$ | CH | F |
| 2-5 | H | H | H | $SOCF_3$ | H | $NCH_3$ | N | F |
| 2-6 | H | $CF_3$ | H | $SCF_3$ | H | $NCH_3$ | N | F |
| 2-7 | H | H | H | $SO_2CF_3$ | H | $NCH_3$ | N | F |
| 2-8 | H | H | H | $CF_2CF_3$ | H | $NCH_3$ | N | F |
| 2-9 | H | H | H | $OCF_3$ | H | $NCH_3$ | N | F |
| 2-10 | H | H | H | $CF_3$ | H | S | CH | F |
| 2-11 | H | $CF_2CF_3$ | H | $CF_3$ | H | $NCH_3$ | N | F |
| 2-12 | H | $CF_2CF_3$ | H | $CF_2CF_3$ | H | $NCH_3$ | N | F |
| 2-13 | H | H | H | $CF_3$ | H | O | N | F |
| 2-14 | H | H | H | $CF_3$ | H | O | CH | F |
| 2-15 | H | $CF_3$ | H | $CF_3$ | CN | $NCH_3$ | N | F |
| 2-16 | H | H | H | $CF_2CF_3$ | H | O | N | F |
| 2-17 | H | H | H | $CF_2CF_3$ | H | O | CH | F |
| 2-18 | H | H | H | $SO_2CF_3$ | H | O | CH | Cl |
| 2-19 | H | H | H | $SOCF_3$ | H | O | CH | Cl |
| 2-20 | H | H | H | $SCF_3$ | H | O | CH | Cl |
| 2-21 | H | $CF_3$ | H | $CF_2CF_3$ | H | $NCH_3$ | N | Cl |
| 2-22 | H | H | H | $CF_3$ | H | $NCH_3$ | N | Cl |
| 2-23 | H | $CF_3$ | H | $CF_3$ | H | $NCH_3$ | N | Cl |
| 2-24 | H | H | H | $SO_2CF_3$ | H | $NCH_3$ | N | Cl |
| 2-25 | H | H | H | $SOCF_3$ | H | $NCH_3$ | N | Cl |
| 2-26 | H | H | H | $SCF_3$ | H | $NCH_3$ | N | Cl |
| 2-27 | H | $CF_3$ | H | $SO_2CF_3$ | H | $NCH_3$ | N | Cl |
| 2-28 | H | H | H | $CF_2CF_3$ | H | $NCH_3$ | CH | Cl |
| 2-29 | H | H | H | $OCF_3$ | H | $NCH_3$ | CH | Cl |
| 2-30 | H | H | H | $CF_3$ | H | S | CH | Cl |
| 2-31 | H | $CF_2CF_3$ | H | $CF_3$ | H | $NCH_3$ | N | Cl |
| 2-32 | H | $CF_2CF_3$ | H | $CF_2CF_3$ | H | $NCH_3$ | N | Cl |
| 2-33 | H | H | H | $CF_3$ | H | O | CH | Cl |
| 2-34 | H | $CF_3$ | H | $CF_3$ | CN | $NCH_3$ | N | Cl |
| 2-35 | H | $CF_3$ | H | $CF_2CF_3$ | H | $NCH_3$ | N | Cl |
| 2-36 | H | $CF_3$ | H | $CF_2CF_3$ | H | $NCH_3$ | N | Cl |
| 2-37 | H | $CF_3$ | H | $CF_2CF_3$ | H | $NCH_3$ | N | Cl |
| 2-38 | H | H | H | $CF_2CF_3$ | H | O | N | Cl |
| 2-39 | H | H | H | $CF_2CF_3$ | H | O | CH | Cl |

$R^1$ represents preferably a chain hydrocarbon group having one to six carbons, more preferably an alkyl group having one to six carbons, and even more preferably a methyl group or an ethyl group.

$M^+$ represents preferably a sodium ion.

Examples of the compound represented by formula (3) (hereinafter, referred to as "Compound (3)") include sodium sulfinates such as sodium methanesulfinate, sodium ethanesulfinate, sodium propanesulfinate, sodium tert-butanesulfinate and sodium pentanesulfinate; and lithium sulfinates such as lithium methanesulfinate, lithium ethanesulfinate, lithium propanesulfinate, lithium butanesulfinate and lithium pentanesulfinate.

Examples of the Compound (3) include preferably sodium sulfinates, and more preferably sodium methanesulfinate and sodium ethanesulfinate.

Compound (3) may be commercially available or may be prepared by reacting a compound represented by formula (4):

(4)

wherein $R^1$ has the same meanings as defined above, and X represents a halogen atom (hereinafter, referred to as "Compound (4)") with a base and a reducing agent.

Examples of the halogen atom defined as X include a fluorine atom, a chlorine atom, a bromine atom, or an iodine atom, and preferably a chlorine atom.

Examples of the Compound (4) include methanesulfonyl chloride, ethanesulfonyl chloride, propanesulfonyl chloride, methanesulfonyl bromide, ethanesulfonyl bromide, and propanesulfonyl bromide.

Examples of the base include alkali metal hydrogen carbonates such as sodium hydrogen carbonate, lithium hydrogen carbonate and potassium hydrogen carbonate; alkali metal carbonates such as sodium carbonate and potassium carbonate; and alkali metal phosphates such as dipotassium hydrogen phosphate.

Examples of the reducing agent include alkali metal sulfites such as sodium sulfite, potassium sulfite and lithium sulfite.

A used amount of the base is usually 2 to 4 moles as opposed to 1 mol of Compound (4), and preferably 2 to 3 moles.

A used amount of the reducing agent is usually 1 to 3 moles as opposed to 1 mol of Compound (4), and preferably 1 to 2 moles.

The reaction of Compound (2) and Compound (3) are usually achieved by mixing Compound (2) and Compound (3). In the mixing step, Compound (3) may be added to Compound (2), or Compound (2) may be added to Compound (3), and Compound (3) may be added at once or in parts.

A used amount of Compound (3) is usually 1 to 10 moles as opposed to 1 mol of Compound (2), and preferably 1 to 2 moles.

Compound (2) and Compound (3) are preferably reacted in the presence of a solvent.

Examples of the solvent include water; aromatic hydrocarbon solvents such as benzene, chlorobenzene and toluene; halogen-containing hydrocarbon solvents such as chloroform and dichloromethane; alcohol solvents such as methanol, ethanol and normal-butanol; ether solvents such as 1,2-dimethoxyethane, diethylene glycol dimethyl ether, polyethylene glycol, tetrahydrofuran and dioxane; nitrile solvents such as acetonitrile and propylnitrile; sulfoxide solvents such as dimethylsulfoxide; amide solvents such as N,N-dimethylformamide, N,N-dimethylacetamlde and N-methylpyrrolidone; and mixture solvents thereof, and include preferably sulfoxide solvents or amide solvents.

A used amount of the solvent is typically 1 to 100 parts by mass as opposed to 1 part by mass of Compound (2).

Compound (2) and Compound (3) may be reacted in the presence of a phase transfer catalyst.

Examples of the phase transfer catalyst include quaternary ammonium salts such as tetrabutylammonium chloride, tetrabutylammonium bromide, tetrabutylammonium iodide and benzyltributylammonium bromide; and quaternary phosphonium salts such as heptyltriphenylphosphonium bromide and tetraphenylphosphonium bromide, and include preferably quaternary ammonium salts and more preferably tetrabutylanmmonium chloride.

A used amount of the phase transfer catalyst is usually 0.01 to 10 moles as opposed to 1 mol of Compound (2), preferably 0.1 to 0.5 moles.

A temperature for reacting Compound (2) and (3) is typically 60 to 150° C., and preferably 80 to 120° C.

A period for reacting Compound (2) and (3) is typically 0.1 to 100 hours, and preferably 3 to 24 hours.

The resulting reaction mixture can be, for example, concentrated to obtain the compound represented by formula (1) (hereinafter, referred to as "Compound (1)"). The obtained Compound (1) can be as needed purified with a conventional purification means such as washing.

Compound (1) is recited as the compounds represented by the formulae (1-1) to (1-23) in Table 2.

TABLE 2

| Compound | $R^1$ | $R^2$ | $R^3$ | $R^4$ | $R^5$ | $R^6$ | $A^1$ | $A^2$ |
|---|---|---|---|---|---|---|---|---|
| 1-1 | $C_2H_5$ | H | H | H | $SO_2CF_3$ | H | O | CH |
| 1-2 | $C_2H_5$ | H | H | H | $SOCF_3$ | H | O | CH |
| 1-3 | $C_2H_5$ | H | H | H | $SCF_3$ | H | O | CH |
| 1-4 | $C_2H_5$ | H | $CF_3$ | H | $CF_2CF_3$ | H | $NCH_3$ | N |
| 1-5 | $C_2H_5$ | H | H | H | $CF_3$ | H | $NCH_3$ | N |
| 1-6 | $C_2H_5$ | H | $CF_3$ | H | $CF_3$ | H | $NCH_3$ | N |
| 1-7 | $C_2H_5$ | H | H | H | $SCF_3$ | H | $NCH_3$ | N |
| 1-8 | $C_2H_5$ | H | H | H | $SO_2CF_3$ | H | $NCH_3$ | N |
| 1-9 | $C_2H_5$ | H | H | H | $SOCF_3$ | H | $NCH_3$ | N |
| 1-10 | $C_2H_5$ | H | $CF_3$ | H | $SO_2CF_3$ | H | $NCH_3$ | N |
| 1-11 | $C_2H_5$ | H | H | H | $CF_2CF_3$ | H | $NCH_3$ | CH |
| 1-12 | $C_2H_5$ | H | H | H | $OCF_3$ | H | $NCH_3$ | CH |
| 1-13 | $C_2H_5$ | H | H | H | $CF_3$ | H | S | CH |
| 1-14 | $C_2H_5$ | H | $CF_2CF_3$ | H | $CF_3$ | H | $NCH_3$ | N |
| 1-15 | $C_2H_5$ | H | $CF_3CF_3$ | H | $CF_2CF_3$ | H | $NCH_3$ | N |
| 1-16 | $C_2H_5$ | H | H | H | $CF_3$ | H | O | N |
| 1-17 | $C_2H_5$ | H | H | H | $CF_3$ | H | O | CH |
| 1-18 | $C_2H_5$ | H | $CF_3$ | H | $CF_3$ | CN | $NCH_3$ | N |
| 1-19 | $CH_3$ | H | $CF_3$ | H | $CF_2CF_3$ | H | $NCH_3$ | N |
| 1-20 | $CH_3(CH_2)_2$ | H | $CF_3$ | H | $CF_2CF_3$ | H | $NCH_3$ | N |
| 1-21 | $(CH_3)_2CH$ | H | $CF_3$ | H | $CF_2CF_3$ | H | $NCH_3$ | N |
| 1-22 | $C_2H_5$ | H | H | H | $CF_2CF_3$ | H | O | CH |
| 1-23 | $C_2H_5$ | H | H | H | $CF_2CF_3$ | H | O | N |

Compound (2) can be, prepared by an intramolecular condensation reaction of the compound represented by formula (7) (hereinafter, often referred to as "Compound (7)"):

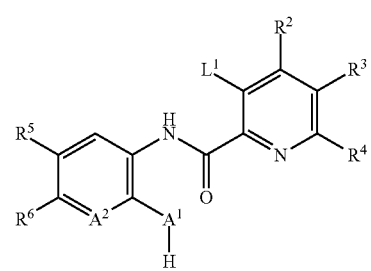

wherein $A^1$, $A^2$, $R^2$, $R^3$, $R^4$, $R^5$, $R^6$, and $L^1$ have the same meanings as defined above, according to the disclosure of WO 2013/018928.

Compound (7) is recited as the compounds represented by the formulae (7-1) to (7-10) in Table 3.

TABLE 3

| Compound | $R^2$ | $R^3$ | $R^4$ | $R^5$ | $R^6$ | $A^1$ | $A^2$ | $L^1$ |
|---|---|---|---|---|---|---|---|---|
| 7-1 | H | H | H | $SOCF_3$ | H | O | CH | F |
| 7-2 | H | H | H | $SCF_3$ | H | O | CH | F |
| 7-3 | H | $CF_3$ | H | $CF_2CF_3$ | H | $NCH_3$ | N | F |
| 7-4 | H | H | H | $CF_3$ | H | S | CH | F |
| 7-5 | H | $CF_3$ | H | $CF_3$ | CN | $NCH_3$ | N | F |
| 7-6 | H | H | H | $SOCF_3$ | H | O | CH | Cl |
| 7-7 | H | H | H | $SCF_3$ | H | O | CH | Cl |
| 7-8 | H | $CF_3$ | H | $CF_2CF_3$ | H | $NCH_3$ | N | Cl |
| 7-9 | H | H | H | $CF_3$ | H | S | CH | Cl |
| 7-10 | H | $CF_3$ | H | $CF_3$ | CN | $NCH_3$ | N | Cl |

The intramolecular condensation reaction of Compound (7) is usually achieved by mixing Compound (7) and an acid.

Examples of the acid include sulfonic acids such as para-toluenesulfonic acid; carboxylic acids such as acetic acid; and polyphosphoric acids.

A used amount of the acid is usually 0.1 to 5 moles as opposed to 1 mol of Compound (7).

A temperature for the intramolecular condensation reaction is typically 0 to 200° C., and a period for the intramolecular condensation reaction is typically 0.1 to 24 hours.

The intramolecular condensation reaction is usually performed in a solvent. Examples of the solvent include ether solvents such as tetrahydrofuran, ethylene glycol dimethyl ether, tert-butyl methyl ether and 1,4-dioxane; aliphatic hydrocarbon solvents such as hexane, heptane and octane; aromatic hydrocarbon solvents such as toluene and xylene; halogenated hydrocarbon solvents such as chlorobenzene; ester solvents such as ethyl acetate and butyl acetate; nitrile solvents such as acetonitrile; aprotic polar solvents such as N,N-dimethylformamide and N,N-dimethylformamide, and mixture solvents thereof. The solvent is preferably aromatic hydrocarbon solvents, and more preferably xylene.

A used amount of the solvent is typically 1 to 100 parts by mass as opposed to 1 part by mass of Compound (7).

The resulting reaction mixture can be, for example, concentrated to obtain the compound represented by formula (2). The obtained Compound (2) can be purified by washing, recrystallization, chromatography, etc.

Compound (7) can be prepared by reacting a compound represented by formula (5) (hereinafter, often referred to as "Compound (5)"):

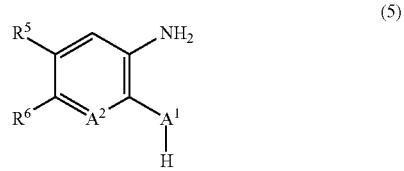

(5)

wherein $A^1$, $A^2$, $A^3$, $R^5$, and $R^6$ have the same meanings as defined above,
with a compound represented by formula (6) (hereinafter, often referred to as "Compound (6)"):

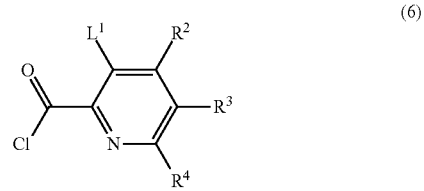

(6)

wherein $R^2$, $R^3$, $R^4$, and $L^1$ have the same meanings as defined above.

Compound (5) is recited as the compounds represented by the formulae (5-1) to (5-8) in Table 4.

TABLE 4

| Compound | $R^2$ | $R^3$ | $A^1$ | $A^2$ |
|---|---|---|---|---|
| 5-1 | SOCF$_3$ | H | O | CH |
| 5-2 | SCF$_3$ | H | O | CH |
| 5-3 | CF$_3$ | H | NCH$_3$ | CH |
| 5-4 | CF$_3$ | H | NCH$_3$ | N |
| 5-5 | CF$_2$CF$_3$ | H | NCH$_3$ | CH |

TABLE 4-continued

| Compound | $R^2$ | $R^3$ | $A^1$ | $A^2$ |
|---|---|---|---|---|
| 5-6 | CF$_2$CF$_3$ | H | NCH$_3$ | H |
| 5-7 | CF$_3$ | H | S | CH |
| 5-8 | CF$_3$ | CN | NCH$_3$ | CH |

Compound (6) is recited as the compounds represented by the formulae (6-1) to (6-4) in Table 5.

A used amount of Compound (6) is usually 1 to 3 moles as opposed to 1 mol of Compound (5).

TABLE 5

| Compound | $R^2$ | $R^3$ | $R^4$ | $L^1$ |
|---|---|---|---|---|
| 6-1 | H | H | H | F |
| 6-2 | H | CF$_3$ | H | F |
| 6-3 | H | H | H | Cl |
| 6-4 | H | CF$_3$ | H | Cl |

Compound (5) and Compound (6) are usually reacted by mixing Compound (5) and Compound (6). Mixing Compound (5) and Compound (6) is preferably performed by adding Compound (6) to Compound (5).

A temperature for the reaction is typically −20 to 100° C., and a period for the reaction is typically 0.1 to 24 hours.

Compound (5) and Compound (6) are usually reacted in a solvent. Examples of the solvent includes the same solvent as used in the intramolecular condensation reaction of Compound (7), include preferably ether solvents, and more preferably tetrahydrofuran.

A used amount of the solvent is usually 1 to 100 parts by mass as opposed to 1 part by mass of Compound (5).

Compound (5) and Compound (6) are usually reacted in the presence of a base. Examples of the base include alkali metal carbonates such as sodium carbonate and potassium carbonate; tertiary amines such as triethylamine and diisopropylethylamine; and nitrogen-containing aromatic compounds such as 4-dimethylaminopyridine.

A used amount of the base is usually 1 to 10 moles as opposed to 1 mol of Compound (5).

The resulting reaction mixture can be, for example, concentrated to obtain Compound (7). The obtained Compound (7) can be purified by chromatography, recrystallization, etc.

EXAMPLES

Preparation Example 1

To a 4-neck flask, sodium sulfite (53.9 g), sodium hydrogen carbonate (65.34 g), and water (325 ml) were added at room temperature under nitrogen atmosphere. After the mixture was stirred at 80° C. for 1.3 hours, ethanesulfonyl chloride (50.0 g) was add thereto, and the mixture was then stirred for an additional 4.2 hours. The reaction mixture was concentrated, and to the resulting residue was added ethanol, and the mixture was further concentrated. To the resulting residue was added toluene, and the mixture was concentrated and the resulting solid was dried, and then thereto was added ethanol (100 ml), and the mixture was heated under reflux. The resulting mixture was filtered and washed with ethanol. The filtrate and wash solution were combined and concentrated to give 38.96 g of sodium ethanesulfinate.

Preparation Example 2

To a 4-neck flask, 2-amino-4-[(trifluoromethyl)sulfinyl] phenol (2.79 g) and dehydrated tetrahydrofuran (38.0 ml)

were added at room temperature under nitrogen atmosphere. The mixture was ice-cooled, and a tetrahydrofuran solution (10.0 ml) containing 3-chloropyridine-2-carbonyl chloride (1.62 g) was added dropwise thereto, and the mixture was stirred at room temperature for 80 minutes. The resulting reaction mixture was adjusted to pH 8 by adding water, saturated aqueous sodium bicarbonate solution, and saturated aqueous ammonium chloride solution. The resulting mixture was extracted with ethyl acetate. The organic layer was washed with saturated aqueous sodium bicarbonate solution, water, and brine sequentially. After the resulting organic layer was dried and concentrated, the resulting solid was dried to give 3.66 g of the mixture containing 3-chloro-N-(2-hydroxy-5-[(trifluoromethyl)sulfinyl]phenyl)pyridine-2-carboxyamide. The mixture was purified with silica gel column (ethyl acetate:hexane=1:1) to give a solid (0.40 g), and the solid was dissolved in ethyl acetate and washed with hydrochloric acid. The resulting ethyl acetate solution was concentrated and dried to give 0.34 mg of 3-chloro-N-{2-hydroxy-5-[(trifluoromethyl)sulfinyl]phenyl}pyridine-2-carboxyamide.

Preparation Example 3

To a 2-neck flask, 3-chloro-N-{2-hydroxy-5-[(trifluoromethyl)sulfinyl]phenyl}pyridine-2-carboxyamide (0.28 g) prepared in Preparation Example 2, xylene (4.0 ml), and p-toluenesulfonic acid monohydrate (0.30 g) were added at room temperature under nitrogen atmosphere. After the mixture was stirred at 140° C. for 3 hours and then cooled to room, temperature, saturated aqueous sodium bicarbonate solution and ethyl acetate were added thereto, and the mixture was then extracted. The organic layer was washed with saturated aqueous sodium bicarbonate solution, water, and brine, and then concentrated to give 0.24 g of the mixture containing 2-(3-chloropyridin-2-yl)-5-(trifluoromethylsulfinyl) benzoxazole. The mixture was purified with silica gel column (ethyl acetate:hexane=56:44 elusion) to give 0.091 g of 2-(3-chloropyridin-2-yl)-5-(trifluoromethylsulfinyl)benzoxazole.

Example 1

To a test tube, 2-(3-chloropyridin-2-yl)-5-(trifluoromethylsulfinyl)benzoxazole (90.3 mg) obtained in Preparation Example 3, sodium ethanesulfinate (45.6 mg) obtained in Preparation Example 1, tetrabutylammonium chloride (22.7 mg), and N,N-dimethylacetamide (4.0 ml) were added at room temperature under nitrogen atmosphere. The mixture was stirred at 105° C. under nitrogen atmosphere for about 23 hours and cooled to room temperature, and water and ethyl acetate were added thereto, and the mixture was partitioned between organic layer and aqueous layer. The aqueous layer was extracted with ethyl acetate, and the resulting ethyl acetate layer and the previously obtained organic layer were combined. The mixture was washed with brine and dried, and then concentrated under reduced pressure to give 90 mg of 2-(3-ethylsulfonylpyridin-2-yl)-5-(trifluoromethylsulfinyl)benzoxazole.

Example 2

To a test tube, 2-(3-chloropyridin-2-yl)-5-(trifluoromethylsulfinyl)benzoxazole (50.2 mg) obtained in Preparation Example 3, sodium ethanesulfinate (26.2 mg), tetrabutylammonium chloride (12.6 mg), and N,N-dimethylacetamide (2.2 ml) were added at room temperature under nitrogen atmosphere. The mixture was stirred at 105° C. under nitrogen atmosphere for about 13 hours, and then sodium ethanesulfinate (13.2 mg) obtained in Preparation Example 1 was added thereto. The mixture was further stirred at 105° C. for 4 hours to give the mixture containing 2-(3-ethylsulfonylpyridin-2-yl)-5-(trifluoromethylsulfinyl)benzoxazole.

Example 3

To a test tube, 2-(3-chloro-5-trifluoromethyl-pyridin-2-yl)-3-methyl-6-pentafluoroethyl-3H-imidazo[4,5-b]pyridine (431 mg), tetrabutylammonium chloride (83 mg), sodium ethanesulfinate (174 mg), and N,N-dimethylacetamide (2.5 ml) were added at room temperature under nitrogen atmosphere. The mixture was stirred at 100° C. tinder nitrogen atmosphere for 4 hours, and cooled to room temperature, and then water and ethyl acetate were added thereto, and the mixture was partitioned between organic layer and aqueous layer. The aqueous layer was extracted with ethyl acetate, and the resulting ethyl acetate layer and the previously obtained organic layer were combined. The mixture was washed with brine and dried, and then concentrated under reduced pressure, and the resulting residue was subjected to silica gel chlomatography to give 453 mg of 2-(3-ethylsulfonyl-5-trifluoromethyl-pyridin-2-yl)-3-methyl-6-pentafluoroethyl-3H-imidazo[4,5-b]pyridine.

INDUSTRIAL APPLICABILITY

The present invention can prepare a compound represented by formula (1) which is useful as an insecticidal agent.

The invention claimed is:

1. A method for preparing a pyridine compound of formula (1):

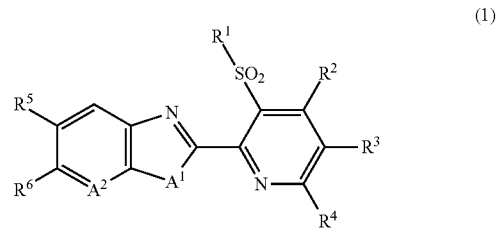

which comprises reacting a compound of formula (2):

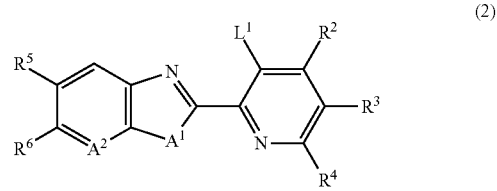

wherein
$L^1$ represents a halogen atom,
$R^2$, $R^3$, $R^4$, $R^5$, and $R^6$ represent each independently a chain hydrocarbon group having one to six carbons which may be optionally substituted with fluorine atom(s), a phenyl group which may optionally have substituent(s), $-OR^{10}$, $-S(O)_mR^{10}$, $-S(O)_2NR^{11}R^{12}$, $-NR^{10}R^{13}$, $-NR^{11}CO_2R^{13}$, $-NR^{11}C$ (O)$R^{12}$, —$CO_2R^{10}$, —C(O)$R^{11}$, —C(O)$NR^{11}R^{12}$, —$SF_5$, a cyano group, a nitro group, or a hydrogen atom, m and n are each independently an integer of 0-2, provided that both $R^5$ and $R^6$ are not a hydrogen atom, $R^{10}$ and $R^{13}$ represent each independently a chain hydrocarbon group having one to six carbons which may be optionally substituted with fluorine atom(s) or a phenyl group which may optionally have substituent(s), $R^{11}$ and $R^{12}$ represent each independently a chain hydrocarbon group having one to six carbons which may be optionally substituted with fluorine atom(s), a phenyl group which may optionally have substituent(s), or a hydrogen atom, $A^1$ represents —$NR^7$—, an oxygen atom, or a sulfur atom, $A^2$ represents a nitrogen atom or =$CR^8$—, and $R^7$ and $R^8$ represent each independently a chain hydrocarbon group having one to six carbons, or a hydrogen atom, wherein in the phenyl group which may optionally have substituent(s) as $R^2$, $R^3$, $R^4$, $R^5$, $R^6$, $R^{10}$, $R^{11}$, $R^{12}$, and $R^{13}$, the substituent(s) is/are one or more substituent(s) selected from the group consisting of a chain hydrocarbon group having one to six carbons which may be optionally substituted with fluorine atom(s), an alkoxy group having one to six carbons which may be optionally substituted with fluorine atom(s), an alkylthio group having one to six carbons which may be optionally substituted with fluorine atom(s), an alkylsulfinyl group having one to six carbons which may be optionally substituted with fluorine atom(s), an alkylsulfonyl group having one to six carbons which may be optionally substituted with fluorine atom(s), an alkylcarbonyl group having two to six carbons which may be optionally substituted with fluorine atom(s), an alkoxycarbonyl group having two to six carbons which may be optionally substituted with fluorine atom(s), a halogen atom, a cyano group, and a nitro group, with a compound of formula (3):

wherein $R^1$ represents a chain hydrocarbon group having one to six carbons which may be optionally substituted with fluorine atom(s) or an alicyclic hydrocarbon group having three to six carbons which may be optionally substituted with fluorine atom(s), and $M^+$ represents a sodium ion, a potassium ion, or a lithium ion, to prepare the compound of formula (1), wherein $R^1$, $R^2$, $R^3$, $R^4$, $R^5$, $R^6$, $A^1$, $A^2$, and $A^3$ have the same meanings as defined above.

2. The method described in claim 1, wherein $R^2$ and $R^4$ represent a hydrogen atom, $R^3$ represents a hydrogen atom or a trifluoromethyl group, $R^5$ represents a trifluoromethyl group, a tetrafluoroethyl group, a trifluoromethylthio group, a trifluoromethylsulfinyl group, or a trifluoromethylsulfonyl group, $R^6$ represents a hydrogen group, and $A^2$ represents a nitrogen atom or =CH—.

3. The method described in claim 2, wherein $A^1$ represents an oxygen atom, and $A^2$ represents =CH—.

4. The method described in claim 2, wherein $A^1$ represents —$NR^7$—, $R^7$ represents a methyl group, and $A^2$ represents a nitrogen atom.

5. The method described in claim 3, wherein $R^1$ represents a chain hydrocarbon group having one to six carbons.

6. The method described in claim 4, wherein $R^1$ represents a chain hydrocarbon group having one to six carbons.

7. The method described in claim 1, wherein $L^1$ represents a fluorine atom or a chlorine atom.

\* \* \* \* \*